United States Patent [19]

Kane et al.

[11] 4,362,580
[45] Dec. 7, 1982

[54] FURNACE AND METHOD WITH SENSOR

[75] Inventors: William T. Kane; William P. Whitney, II, both of Big Flats, N.Y.

[73] Assignee: Corning Glass Works, Corning, N.Y.

[21] Appl. No.: 251,535

[22] Filed: Apr. 6, 1981

Related U.S. Application Data

[62] Division of Ser. No. 118,479, Feb. 4, 1980, Pat. No. 4,290,586.

[51] Int. Cl.³ .............................................. C21D 1/48
[52] U.S. Cl. ..................................... 148/16; 148/20.3; 73/23
[58] Field of Search ....................... 266/80, 81, 87, 90, 266/88, 251; 204/195 S; 432/37, 42; 73/23; 324/425; 118/479; 148/16, 16.5, 16.6, 16.7, 20.3

[56] References Cited

U.S. PATENT DOCUMENTS 4,145,232 3/1979 Solomon ............................ 148/16.5

4,168,186 9/1979 Limque et al. ..................... 148/20.3

OTHER PUBLICATIONS

Beach, N. "Practical Experience in the Control of Heat Treatment Atmospheres using Oxygen Probe," 5th Industrial Process Heating Conference, Birmingham 1972.

Primary Examiner—John P. Sheehan
Attorney, Agent, or Firm—Richard N. Wardell

[57] ABSTRACT

Oxygen sensor comprising solid oxygen-ion-conducting electrolyte with a platinum group metal film electrode contacts and monitors nonoxidizing or reducing gas atmosphere in a metal heat treatment (gas carburizing) furnace after a getter of the same platinum group metal as in the film electrode removes platinum group metal contaminants from such atmosphere before it contacts the electrode. Getter is held in a thin-walled, multi-passaged honeycomb body.

6 Claims, 4 Drawing Figures

FURNACE AND METHOD WITH SENSOR

CROSS-REFERENCE TO RELATED APPLICATION

This is a division of application Ser. No. 118,479, filed Feb. 4, 1980, now U.S. Pat. No. 4,290,586.

U.S. Application Ser. No. 118,480 of William T. Kane entitled OXYGEN SENSOR, filed Feb. 4, 1980 (now U.S. Pat. No. 4,290,586) to the same assignee as was the present application, discloses and claims the invention pertaining to the porous ceramic boot 44 disclosed herein.

BACKGROUND OF THE INVENTION

This invention relates to an improvement in the use of the known type of oxygen sensor comprising a solid oxygen-ion-conducting electrolyte with porous, thin layer or film, metal (e.g. platinum) electrodes attached on substantially opposite surfaces of the electrolyte. When each electrode of this type of sensor is in contact with a different oxygen concentration and the electrodes are connected in an electrical measuring circuit, oxygen ions migrate through the electrolyte between the electrodes coincidently with a flow of electrons in the circuit generating a measurable voltage or electromotive force between (or across) the electrodes or two points in the circuit.

This type of sensor has been known for use in monitoring: (1) exhaust gases of internal combustion engines in thermodynamic nonequilibrium for control of the air-fuel ratio in the combustion process, (2) stack or flue gases of industrial combustion furnaces for control of the combustion process to eliminate smoke and other undesirable emissions, and (3) furnace atmospheres of metal heat treating and other furnaces in substantial thermodynamic equilibrium for control of their oxygen potential, e.g. in nonoxidizing and reducing gas atmospheres.

However, durability of the thin layer or film platinum electrode in contact with the monitored flowing hot gases has been a problem. Such electrode has been variously noted to be adversely affected by thermal shock and differential expansion stresses in the sensor, mechanical abrasion and impact stresses caused by particles carried in the flowing gases, and chemical reaction effects with constituents in the gases being monitored.

The presence of metal vapors in nonoxidizing or reducing atmospheres of metal heat treating furnaces have been noted in U.S. Pat. No. 3,645,875 to cause alloying with and embrittlement of the platinum film electrode which does not serve any catalytic function in this environment. In conjunction with the reducing conditions at high temperatures, the bond (and electrical continuity) between such electrode and the solid electrolyte is also noted to be adversely affected. Of course, it has been known for some time (see Metals Handbook, 8th Edition, Vol. 1, pp. 1178 and 1190, published 1961 by the American Society for Metals) that platinum in hot reducing atmospheres is attacked and contaminated by phosphorus, arsenic, lead, bismuth, antimony, silicon, iron and manganese. Moreover, in our recent studies of platinum film electrodes tested in contact with operating atmospheres of steel carburizing furnaces, we discovered the principal platinum alloying contaminant to be zinc, although other contaminants found included iron, titanium, nickel, boron, lead, chromium, sodium and copper.

The remedy suggested by U.S. Pat. No. 3,645,875 for the problem of platinum contaminants in reducing atmospheres is to adherently attach a porous, thin, protective overlayer on the platinum film electrode, which overlayer is formed of refractory material such as zirconia. A similar remedy for mechanical and chemical damages to platinum film electrodes exposed to automotive exhaust gases is proposed in U.S. Pat. No. 3,978,006. However, U.S. Pat. No. 4,164,462 notes that such overlayers can suffer a durability problem (cracking) of their own. The latter fact was confirmed in our own studies, which showed that such overlayers (e.g. of alumina cement) readily crack and spall off, thereby leaving significant portions of the platinum film electrode unprotected. The further consequence of the foregoing results was embrittled (mainly by zinc alloying) and cracked platinum film electrodes such that those electrodes could easily be removed from the electrolyte by scraping with a finger nail. Additionally, trying to improve the strength and adherence of the overlayer by firing it at higher temperatures above about 1150° C. is often unsatisfactory, especially for sensors with stabilized zirconia electrolytes to be used in metal heat treating processes. Besides the possibility of destroying the needed porosity by sintering the overlayer too dense, reheating of the stabilized zirconia electrolyte (while firing the overlayer) above about 1150° C. causes a change in the zirconia structure, which in turn causes the electrolyte to exhibit sluggish nonideal behavior in service at temperatures below about 1150° C. as is often the case in metal heat treating processes.

With respect to monitoring internal combustion engine exhaust gases with sensors of the type described above, U.S. Pat. No. 4,021,326 notes the problem of catalyst poisons which interfere with the catalytic activity of the catalytic (e.g. platinum) film electrode. Such activity is needed to catalyze the formation of thermodynamically stable gases (i.e. gases in thermodynamic equilibrium) from the nonequilibrium exhaust gases prior to contacting the electrolyte with such stable gases. The remedy suggested by this patent for such poison problem is the application of a getter for the catalytic poisons in or on top of the thin, porous, protective layer covering the catalytic film electrode. Identified poisons are heavy metals such as lead, copper, zinc, and nonmetals such as sulfur and halogen compounds. Suitable getters for these poisons are noted to be gold, silver, nickel and/or nickel oxide and silicon dioxide. It is to be noted, however, that catalyst poisons are not conceptually nor quantitatively the same as embrittling alloy contaminants of an electrode as noted in U.S. Pat. No. 3,645,875.

Further improvements in oxygen sensor devices for monitoring internal combustion engine exhaust gases have been revealed for supplementing the capacity of the catalytic (platinum) film electrode to promote the needed thermodynamic equilibrium in those gases for more accurate sensor operation. U.S. Pat. Nos. 3,935,089 and 4,097,353 suggest incorporating platinum into the thin-layer, porous, protective coating on the film electrode that is contacted by the monitored gases. U.S. Pat. No. 4,132,615 discloses passing the nonequilibrium exhaust gases through a catalyst mass (such as a bed of alumina pellets containing platinum catalyst) before contacting the oxygen sensor. U.S. Pat. No. 4,140,611 teaches the use of a honeycomb type oxidation catalyzer (otherwise known to contain platinum catalyst) in the same manner as the catalyst mass of the preceding patent.

U.S. Pat. No. 4,121,989 shows a specially tailored oxygen sensor device for greater efficiency, accuracy and reproducible operation in monitoring stack gases from industrial combustion furnaces to control the degree of combustion and combustion efficiency with excess air. Such device has felted ceramic fiber discs partly embedded into fired, thin-layer, paste-derived, platinum electrodes and thermally reduced, high surface area, platinum particles dispersed over the electrode surfaces and within the felted discs as a result of applying chloroplatinic acid through the felted discs to the electrode surfaces. Such particles augment the capacity of the platinum electrodes to effect the ionization-deionization reactions of oxygen in the device.

SUMMARY OF THE INVENTION

This invention is premised upon our recognition and discovery that platinum group metal (e.g. platinum) can and should be employed as a getter of contaminants of such metal (especially zinc contaminant) in nonoxidizing and reducing gas atmospheres of metal heat treating furnaces, when positioned upstream from an oxygen sensor, to protect the film electrode of the sensor made of the same platinum group metal as in the getter and that is to contact such atmosphere for determining and monitoring the oxygen potential of that atmosphere. Our platinum group metal getter significantly extends the life of the oxygen sensor by reacting and alloying with the platinum group metal contaminants and thus removing them from the gas atmosphere stream before those contaminants can damage the film electrode of the same platinum group metal contacted by such stream.

In one aspect, our invention is a furnace for heat treatment of metal workpieces in nonoxidizing (or reducing) gas atmosphere containing platinum group metal contaminants. The furnace comprises:

an enclosure defining a chamber adapted to contain the workpieces and the atmosphere, the enclosure including at least one wall portion having an oxygen sensor device extending therethrough to monitor the oxygen potential of the atmosphere, the sensor device comprising a casing with one portion thereof mounted in an opening in the wall portion and a second portion of the casing protruding into the chamber, the casing having an inlet in the second portion for the atmosphere to continuously enter and flow within the casing from the chamber, an oxygen sensor mounted within the casing with an electroded portion of the sensor intermediate of the inlet and the one portion of the casing, the electroded portion comprising a solid oxygen-ion-conducting electrolyte and a film electrode of platinum group metal attached on a surface of the electrolyte arranged to contact the atmosphere flowing within the casing, and a platinum group metal contaminant getter consisting essentially of the same platinum group metal as in the electrode and arranged in the casing between the inlet and the electroded portion so that the atmosphere passes into contact therewith to effect gettering of the platinum group metal contaminants from the atmosphere.

In another aspect, our invention is a method of heat treating metal workpieces in a nonoxidizing (or reducing) gas atmosphere containing platinum group metal contaminants. The method comprises:

heat treating the workpieces in the atmosphere, during the heat treatment, passing sequential portions of the atmosphere into contact with a platinum group metal contaminant getter consisting essentially of platinum group metal and thereby effecting gettering of the contaminants from those portions, thereafter passing those portions into contact with an electroded portion of an oxygen sensor comprising a solid oxygen-ion-conducting electrolyte with a film electrode of the same platinum group metal as in the getter and attached on a surface of the electrolyte and exposed to those portions whereby the oxygen potential of the atmosphere is monitored for undesirable change in that potential.

The invention also includes our recognition and discovery of a particularly advantageous form for employing platinum group metal as the getter in such heat treating furnace and its operation. That form provides reasonably extended durability and gettering efficiency for the getter without interfering with the capability of the oxygen sensor device to properly monitor the furnace atmosphere for its oxygen potential. The form comprises a thin-walled, multipassaged honeycomb body (preferably of porous ceramic) through whose plurality of passages the furnace atmosphere flows to the oxygen sensor and on (and preferably also within) whose walls the platinum getter is contained and exposed to the atmosphere.

DETAILED DESCRIPTION

Figure 1:
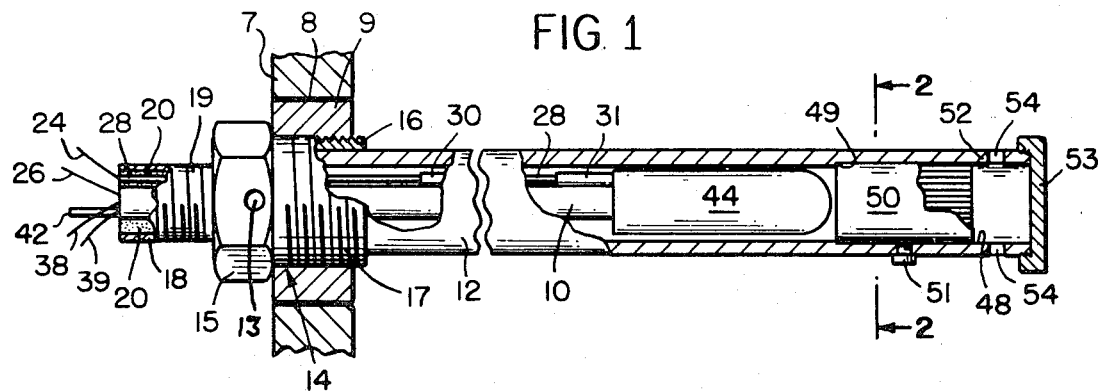
FIG. 1 is a partially sectioned view of a portion of a heat treating furnace enclosure or wall through which is mounted an oxygen sensor device of the present invention.

In FIG. 1, furnace wall 7 defines (in part) the furnace chamber space to the right of such wall. Mounted in an opening in the wall 7, as by welded joint 8, is a collar member 9, whose inner annular surface is threaded in a complementary manner to receive the threads 17 on the larger end portion 16 of the fitting 14 for mounting the oxygen sensor device in and through the wall 7.

The oxygen sensor device comprises an oxygen-ion-conducting solid electrolyte tube 10 positioned inside a protective casing 12. In the preferred embodiment, the solid electrolyte is a yttria-stabilized zirconia containing about 8% $Y_2O_3$ by weight, and casing 12 is made of Inconel alloy. However, any solid oxygen-ion-conducting electrolyte and any suitable heat-resistance metal of the casing can be used. One end of casing 12 is positioned inside the larger bore of fitting 14 so as to fully extend into that bore passing through larger end portion 16 and partly into the hexagonal-shaped middle portion 15 of fitting 14. Three set screws 13 (only one shown), equally spaced around middle portion 15, hold the casing 12 within fitting 14; however, other fastening means can be employed as desired. Screws 13 and fitting 14 are preferably made of stainless steel. Fitting 14 includes a smaller end portion 18 with threads 19 for connection to a terminal structure such as a conventional thermocouple head (not shown). Smaller end portion 18 also has a bore centrally within which the open end of electrolyte tube 10 is fastened by means of a suitable cement 20, such as sauereisen cement.

Figure 2:
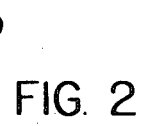
FIG. 2 is a sectional view taken along a line 2—2 in FIG. 1.
Figure 3:
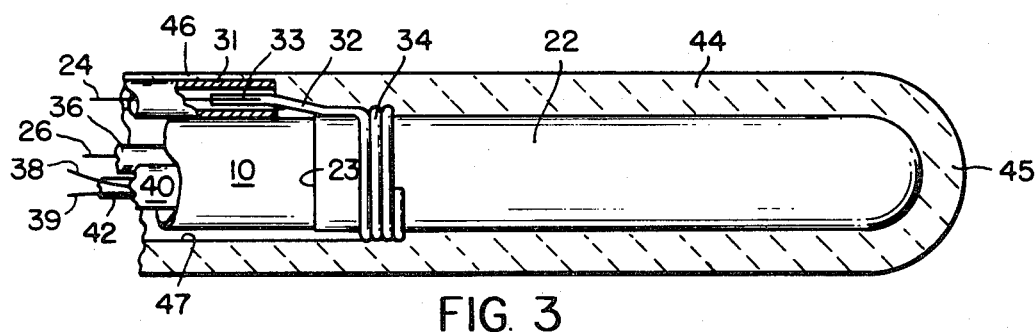
FIG. 3 is an enlarged sectional view of one variation of an oxygen sensor useful in the present invention.

As shown in FIGS. 2 and 3, the closed end of electrolyte tube 10 has an outer platinum film electrode 22 extending over the entire hemispherical end of the tube and on up the tube a short distance to the edge 23 of electrode 22. An inner platinum film electrode (not shown) extends over the portion of the inner bore surface of the tube 10 opposite to that of the outer surface covered by electrode 22 (as is conventional). The platinum film electrodes can be formed by any suitable method, but it is preferred to use a platinum paste which is painted on the desired surfaces and then fired thereon to partially sinter the resulting platinum coating. A particularly desired paste mixture comprises equal parts by weight of platinum resinate paste containing 65.5 wt. % Pt and platinum dust or powder of −325 mesh U.S. Standard Screen, and to 85 parts by weight of which is added 15 parts by weight of lavender oil for providing a paint consistency to the paste mixture. This mixture is applied to a cleaned electrolyte tube surface, dried at about 120° C. for 15 minutes and then fired at about 1150° C. for one hour. This procedure is used for each coating application and usually three coating applications, one on top of the other, are necessary for an adequate thickness of platinum to form the film electrodes. The second and subsequent coatings are usually fired at about 1000° C. for one hour.

By any suitable or conventional means, an outer platinum electrical lead wire 24 is connected to outer electrode 22 and an inner platinum electrical lead wire 26 is connected to the inner electrode (not shown). Typically such wires can be of 12-17 mil diameter sizes. Wire 24 is carried within a single-bore alumina tube 28 extending through casing 12 and fitting 14 to the left end of portion 18. Such tube 28 is also fastened within the bore of portion 18 by means of the cement 20. To accomodate the differing thermal expansions of electrolyte tube 10 and alumina tube 28 while still being able to hold tube 28 to tube 10, short, single-bore, alumina sleeves 30,31 are cemented to tube 10 as shown in FIGS. 1-3 and the tube 28 is slidably held within the bore of sleeves 30,31. Thus tube 28 electrically insulates and physically protects wire 24 without causing any differential thermal expansion stresses in the sensor device.

Figure 4:
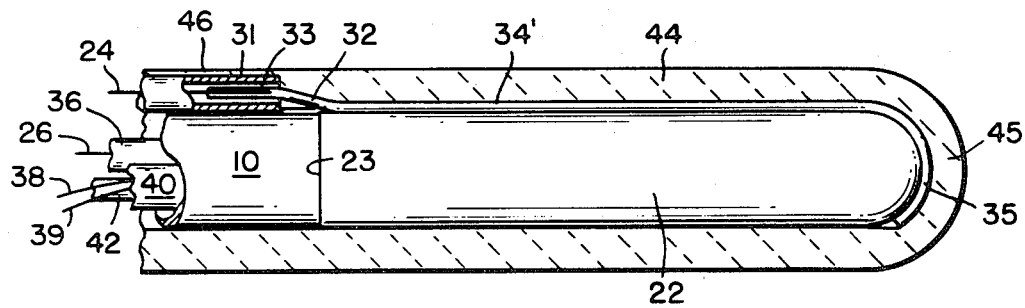
FIG. 4 is an enlarged sectional view of another variation of any oxygen sensor useful in the present invention.

In the preferred embodiment, a platinum connector wire 32 (see FIGS. 2 and 3) is fixed to electrode 22 and spot welded to wire 24 at their overlap junction 33. Wire 32 is preferably thicker than wire 24, e.g. 17-40 mil diameter. In connecting wire 32 to electrode 22, only one fired paste mixture coating is made prior to placing wire 32 on that coating. Wire 32 can be placed on the initial electrode coating in any desired manner, e.g. by coiling a portion 34 around the electrode coating 22 as in FIG. 3 or by molding a portion 34' to extend longitudinally along electrode coating 22 and around its hemispherical end with curved portion 35 of wire 32 as in FIG. 4. After wire 32 is so placed on the initial coating of electrode 22, two additional fired paste mixture coatings are applied over the initial electrode coating 22 and the portions of wire 32 laid thereon. Those fired top coatings of electrode 22 serve to fasten or bond wire 32 to electrode 22 in the position in which it was placed thereon.

Inner lead wire 26 is carried in a single-bore alumina tube 36 from adjacent the inside hemispherical closed end surface of tube 10 (where a small protruding portion of wire 26 is fastened to the inner electrode by any suitable or conventional means) on through the bore of tube 10 to the opposite end thereof.

Also extending through the bore of tube 10 are thermocouple wires 38,39 carried in a double-bore alumina tube 40 and a tube 42 for a reference oxygen gas (e.g. air). These components extend into the bore of tube 10 to a point shortly beyond electrode edge 23 (i.e. between edge 23 and the hemispherical closed end of tube 10). It is in the vicinity of that point at which the thermocouple wires protrude out of tube 40 and are joined in a thermocouple junction and also the reference gas is introduced to the inner electrode from the open end of tube 42. Likewise, these components also extend oppositely to the other end of tube 10, where further extensions of wires 38,39 and tube 42 as well as of wires 24,26 are available for respective appropriate connections to a thermocouple temperature measuring circuit, a gas supply and a voltage measuring circuit, all as is conventional. In order to insure the physical integrity of the components extending within tube 10, it is preferred to cement the ends of tubes 36, 40, 42 within the end of tube 10 fastened in the bore of fitting portion 18; however, care is taken to make sure that the cement does not completely seal the open end of tube 10 so that the reference gas is allowed to exit therefrom.

The main improvement element 50 of the present invention is preferably embodied in an assembly having a porous ceramic boot 44, as claimed in the aforesaid copending application Ser. No. 118,480. It is advantageous to slidably and frictionally engage the compressible, porous, ceramic boot or cover 44 and its hemispherically closed end 45 onto and over electrode 22 and wire 32 to physically hold the electrode 22 and wire 32 in contact with electrolyte 10 even if the platinum of electrode 22 and wire 32 becomes embrittled after an extended period of service and would otherwise tend to separate from contact with the electrolyte tube 10. Boot 44 is made of a sintered, porous, oxide that is thermodynamically stable in the nonoxidizing or reducing atmosphere of the heat treating furnace and is nonreactive with platinum. Preferably such oxide is zirconia which is advantageously in a stabilized form with a stabilizer that is also nonreactive with platinum. Desirably it is yttria-stabilized zirconia with 8 wt.% $Y_2O_3$. The boot 44 should have an open porosity of greater than 50 volume % (preferably greater than 80 volume %) for adequate rapid passage of monitored atmosphere to the electrode 22. In the preferred embodiment, boot 44 is composed of a sintered mass of short 8 wt.% yttria-stabilized zirconia fibers (e.g. 1/16 inch mean length and 4-6 microns diameter) mixed with a minor portion (about 1 wt.%) of submicron zirconia powder stabilized with a similar percentage of yttria. Such mixture is shaped as a boot 44 and fired sufficiently to render the sintered boot to be coherent, substantially firm structure with over 80 vol. % open porosity and yet capable of being grooved or compressed with the manual pressure of a person's fingernail. Thus, such boot 44 can be slidably and firmly pressfit onto tube 10 over electrode 22 and wire 32 whereby the sliding engagement with wire 32 easily grooves or compresses an inner portion of boot 42 just sufficient to accomodate wire 32 therein without otherwise damaging boot 44. It is also advantageous for the boot 44 to extend over the tip of sleeve 31 so as to protect the portion of wire 32 entering sleeve 31. The latter is easily accomodated by sleeve 31 further grooving or compressing the inside of portion 46 of boot 44 just sufficient to accomodate sleeve 31, again without otherwise damaging boot 44. In the case of wire coil 34 (FIG. 3), it compresses the inner diameter 47 of boot 44 to an enlarged size just sufficient to accomodate coil 34.

In accord with our invention claimed herein, it is advantageous to employ a getter 50 upstream from the electroded portion of tube 10. Accordingly in our present invention, me include a honeycomb getter 50 positioned within the portion of casing 12 having a bore 48 of enlarged diameter relative to the remainder of casing 12 whereby the getter 50 is further positioned by shoulder 49 joining the two bore diameters of casing 12. Stainless steel set screw 51 engages and holds getter 50 in its position. Getter 50 comprises a thin-walled honeycomb body with a plurality of passages therethrough for passage of furnace atmosphere to the electroded portion of the oxygen sensor within boot 44. Such honeycomb body is known to cause relatively little backpressure effect against incoming gases thereto, and that minor effect is easily overcome by the positive (i.e. greater than atmospheric) pressure and/or velocities of gas atmosphere flowing in a furnace chamber and entering the getter 50. Preferably the honeycomb getter 50 comprises a ceramic honeycomb body with porous walls containing platinum thereon and desirably within the open pores in the walls. Such honeycomb body can be made by any suitable or known method, such as those described in U.S. Pat. Nos. 3,112,184 and 3,790,654, especially that of the latter patent. Such body can have transverse passage or cell density ranging from about 15 to 900 cells/square inch of transverse cross-section, but preferably of 300 cells/in$^2$. The wall thicknesses can range from about 2 to 50 mils, but preferably is about 10 mils. Wall open porosity is advantageously in the range of 10 to 50 volume %, but preferably at least about 14 vol. %. The ceramic forming the body should be reasonably thermodynamically and physically stable under conditions of hot furnace nonoxidizing atmospheres passing therethrough. Preferably the ceramic consists essentially of two crystal phases: zirconia and magnesium aluminate spinel. The preferred zirconia/spinel weight % ratios range from 65/35 to 30/70, with 60/40 being most preferred. The platinum can be applied to the walls of the honeycomb body in any suitable or known manner. Generally one can employ the conventional technique of impregnating the porous honeycomb body by dipping it in chloroplatinic acid (usually in an aqueous solution of 25 wt. % $H_2PtCl_6$), draining excess solution from gas atmosphere to thermally decompose and reduce the acid to platinum metal residue on the honeycomb body. This dip/fire procedure is repeated about three to four times or so as to obtain a platinum loading of at least about 5 wt.% (and preferably about 10 wt.%) of the platinized honeycomb body. Such platinized honeycomb body with a 2 inch length and a $\frac{5}{8}$ inch diameter has been found quite adequate to provide getter protection for an electroded portion of an electrolyte having a 2 inch length and a $\frac{3}{8}"$ outside diameter.

Comparative tests in gas carburizing furnaces have shown that sensors like those described herein, but not including either boot 44 or getter 50 survived up to 9 weeks service before the sensors failed to properly function. Such sensors protected only with the getter 50 have survived up to more than 53 weeks—almost a 6 fold improvement in service life. The sensors containing the boot 44, but not protected by getter 50, survived up to more than 16 weeks service—a modest improvement despite lack of getter protection. In the case of the sensors protected with both the getter 50 and the boot 44, the survival period has not been well determined yet, but it has extended up to more than 33 weeks without failure (as the service test is continuing).

As is evident from the description herein, the honeycomb getter 50 is a consumable element easily replaced as needed to provide adequate gettering for continued or extended life of the sensor device.

Background information on the operation of oxygen sensors for monitoring oxygen potential in and controlling nonoxidizing or reducing atmospheres of carburizing and other metal heat treating furnaces can be found in the articles by R.G.H. Record in Instrument Practice, March 1970, and Metallurgia and Metal Forming, December 1972/January 1973, both published in Great Britain. These articles are incorporated herein by this reference.

As an option, casing 12 may include a protective extension 52 having a cap 53 threaded onto and closing its end opening, but also having side ports 54 for entrance of furnace atmosphere into casing 12. However, generally the extension 52 is omitted and end the casing 12 at the entrance (right) end of getter 50 with such casing end being open to the furnace atmosphere as an inlet therein. An optional outlet in the casing can be suitably provided and arranged at any point to the left of boot 44 (i.e. the electroded portion of tube 10) for exiting monitored atmosphere either within or outside of the furnace enclosure 7, e.g. by leaving an opening or passage through cement 20 within fitting portion 18 whereby the monitored furnace atmosphere passes completely through the casing 12 and fitting 14 to be suitably exited outside the furnace enclosure 7. However, for use in conventional steel carburizing furnaces wherein the furnace atmospheres are thoroughly circulated, by means of fans, at high velocities such as 200 feet per second, many experimental tests have shown there is no need for a separate outlet from the casing (i.e. separate from the inlet). Thus, the hurricane-like atmosphere condition in the carburizing furnace is sufficiently effective to continuously force new sequential portions of the atmosphere into the sensor device employed in this invention. Of course, the plurality of passages of honeycomb getter 50 and the high porosity of boot 44 facilitate easy access to the electroded portion of tube 10. The strong swirling action of the carburizing furnace atmosphere apparently causes turbulent flow in portions of such atmosphere in casing 12 so as to push them into contact with the electroded portion and then flush them back out of the inlet in order to allow new sequential portions to be pushed into casing 10 for contact with the electroded portion.

Thus, the method of using the above-described sensor involves the heat treatment of metal workpieces in the chamber to the right of wall 7, into which the sensor device protrudes. Sequential portions of nonoxidizing or reducing furnace atmosphere enter the inlet at the right end of casing 12, e.g. the ports 54, and pass through getter 50. After removal of platinum contaminants from those portions of atmosphere by getter 50, the portions continue to flow to and through boot 44 into contact with the electroded portion of electrolyte tube 10 containing electrode 22, wherein the oxygen potential of such atmosphere portions are detected and monitored by the oxygen sensor. Thereafter, such atmosphere portions are flushed out of the casing 12. During this operation of the method, air as a preferred reference gas is flowed into the left end of tube 42, through that tube and into the closed end of the bore within tube 10 where the inner platinum film electrode is located. Thereafter, the air reference gas passes through the bore of tube 10 to exit from its partially open left end.

While the detailed examples have been described herein with illustrative reference to only platinum as getter and film electrode (including connector wire), it should be understood that any other platinum group metal (e.g. palladium, ruthenium, etc.) can be used as desired.

What is claimed is:

1. A method of heat treating metal workpieces in a non-oxidizing gas atmosphere containing platinum group metal contaminants, which method comprises heat treating the workpieces in the atmosphere, during the heat treatment, passing sequential portions of the atmosphere into contact with a platinum group metal contaminant getter consisting essentially of platinum group metal and thereby effecting gettering of the contaminants from those portions, thereafter passing those portions into contact with an electroded portion of an oxygen sensor comprising a solid oxygen-ion-conductive electrolyte with a film electrode of the same platinum group metal as in the getter and attached on a surface of the electrolyte and exposed to those portions whereby the oxygen potential of the atmosphere is monitored for undesirable change in that potential.

2. The method of claim 1 wherein the getter is contained on the walls of a plurality of passages within a thin-walled honeycomb body and the portions of atmosphere are passed through those passages.

3. The method of claim 1 wherein the electrolyte is stabilized zirconia.

4. The method of claim 1 wherein the honeycomb body is of a refractory ceramic.

5. The method of claim 4 wherein the ceramic consists essentially of two crystal phases: zirconia and magnesium aluminate spinel.

6. The method of claim 1 wherein the atmosphere is a reducing gas atmosphere.

* * * * *